United States Patent
Izu et al.

(10) Patent No.: US 7,578,974 B2
(45) Date of Patent: Aug. 25, 2009

(54) RESISTIVE TYPE OXYGEN SENSOR AND AIR/FUEL RATIO CONTROL SYSTEM USING IT

(75) Inventors: Noriya Izu, Aichi (JP); Norimitsu Murayama, Aichi (JP); Woosuck Shin, Aichi (JP); Ichiro Matsubara, Aichi (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 388 days.

(21) Appl. No.: 11/252,721

(22) Filed: Oct. 19, 2005

(65) Prior Publication Data

US 2006/0081473 A1   Apr. 20, 2006

(30) Foreign Application Priority Data

| Oct. 19, 2004 | (JP) | ............................. 2004-304781 |
| Aug. 8, 2005 | (JP) | ............................. 2005-230179 |
| Oct. 13, 2005 | (JP) | ............................. 2005-299417 |

(51) Int. Cl.
*G01N 30/96* (2006.01)

(52) U.S. Cl. ........................................ 422/88
(58) Field of Classification Search .................... 422/88
See application file for complete search history.

(56) References Cited

U.S. PATENT DOCUMENTS 5,985,476 A * 11/1999 Wachsman et al. ............. 429/33
6,513,321 B2 * 2/2003 Suzuki et al. ................. 60/285
2006/0057292 A1 * 3/2006 Izu et al. ................... 427/372.2

FOREIGN PATENT DOCUMENTS

| JP | 55-137334 | 10/1980 |
| JP | 62-174644 | 7/1987 |
| JP | 2004-93547 | 3/2004 |
| WO | WO 2004059308 A1 * | 7/2004 |

OTHER PUBLICATIONS

U.S. Appl. No. 10/571,771, filed Dec. 27, 2004, Noriya Izu, et al.
U.S. Appl. No. 10/540,873, filed Jun. 27, 2005, Noriya Izu, et al.
E.B. Varhegyi, et al., "Auger and Sims study of segregation and corrosion behaviour of some semiconducting oxide gas-sensor materials", Sensors and Actuators B, 18-19, 1994, pp. 569-572.

* cited by examiner

*Primary Examiner*—Walter D Griffin
*Assistant Examiner*—Bobby Ramdhanie
(74) *Attorney, Agent, or Firm*—Oblon, Spivak, McClelland, Maier & Neustadt, P.C.

(57) ABSTRACT

A resistance-type oxygen sensor which is provided to be used mainly for measuring the oxygen gas partial pressure of automobile exhaust gas, and which has a short output response time in response to changes in oxygen partial pressure, low resistivity of the oxide semiconductor, and low temperature dependence of the resistivity.

In a resistance-type oxygen sensor, in which the oxygen gas detection part comprises an oxide semiconductor, the oxide semiconductor is an oxide comprising cerium ions and hafnium ions, the amount of substance of cerium ions as a percentage of the amount of substance of positive ions is 60 mol % or more, the amount of substance of hafnium ions as a percentage of the amount of substance of positive ions is 3 to 30 mol %, and the hafnium ions are an oxide in solid solution in the parent phase.

7 Claims, 10 Drawing Sheets

1··· Substrate
2··· Electrode
3··· Oxygen gas detection part (oxide semiconductor)
4··· Temperature compensation part 1··· Substrate
2··· Electrode
3··· Oxygen gas detection part (oxide semiconductor)
4··· Temperature compensation part

RESISTIVE TYPE OXYGEN SENSOR AND AIR/FUEL RATIO CONTROL SYSTEM USING IT

BACKGROUND OF THE INVENTION

1. Field of the Invention

The present invention relates to a new type of resistance-type oxygen sensor, and relates more specifically to an oxygen sensor for measuring oxygen partial pressure which is used mainly in air-fuel ratio feedback control systems for controlling the air-fuel ratio of automobile exhaust gas in order to improve the purification rate of the exhaust gas as well as fuel consumption for example. In the present invention, new technologies and new products relating to a new type of resistance-type oxygen sensor are provided which is an oxygen sensor having a gas detection part made of an oxide semiconductor, the resistivity of which varies depending on the oxygen partial pressure of the atmospheric gas, and with which a variety of problems with conventional products, such as the high resistivity of oxide semiconductors and high temperature dependence of sensors and the complexity of the circuits, can be fundamentally resolved in the technical field of resistance-type oxygen sensors using oxide semiconductors as oxygen gas detectors which are used as oxygen sensors for automobile exhaust gas.

2. Description of the Related Art

In the past, solid electrolytes have mainly been used as oxygen sensors for automobiles (Japanese Patent Application Laid-open No. S55-137334). This type of sensor measures the difference between the oxygen partial pressures of a reference electrode and a measurement electrode, and always requires a reference electrode. Consequently, the problem with this type of sensor is that the sensor structure is complex, making miniaturization difficult. To resolve this problem, a type of resistance-type oxygen sensor has been developed for example which does not require a reference electrode (Japanese Patent Application Laid-open No. S62-174644).

To give a simple explanation of the measurement principles of this type resistance-type oxygen sensor, first, the oxygen vacancy concentration of the oxide semiconductor varies with the oxygen partial pressure of the atmosphere. In this case, the resistivity or electrical conductivity of the oxide semiconductor is in a 1:1 correlation with the oxygen vacancy concentration, so that the resistivity of the oxide semiconductor changes as the oxygen vacancy concentration changes. Consequently, the oxygen partial pressure of the atmosphere can be known by measuring the resistivity or resistance.

Titanium oxide has conventionally been used as the material for the oxide semiconductor of this resistance-type oxygen sensor, but the problem with this material is that it has poor durability and stability. To fundamentally resolve these problems, the inventors have already researched and developed a resistance-type oxygen sensor using cerium oxide as the oxide semiconductor. This cerium oxide is known to be durable in corrosive gas (see E. B. Varhegyi et al, Sensors and Actuator B, 18-19 (1994) 569). However, a resistance-type oxygen sensor using cerium oxide alone as the oxide semiconductor had the problem that the resistivity thereof was high. If the resistivity is high, the problem that the circuits for measuring the resistance of the oxygen gas detector become more complicated for example is generated. To solve this problem, a resistance-type oxygen sensor was developed using an oxygen gas detection part having a solid solution of cerium oxide added with zirconium oxide as the oxide semiconductor (Japanese Patent Application Laid-open No. 2004-93547).

However, even with this resistance-type oxygen sensor the resistivity of a solid solution of cerium oxide with added zirconium oxide is not low enough, and a new problem is that the resistivity of a solid solution of cerium oxide added with zirconium oxide is actually more temperature dependent than the resistivity of cerium oxide with nothing added. There exists a problem that when temperature dependence is high, output errors increase as the temperature rises.

SUMMARY OF THE INVENTION

Under these circumstances, the inventors discovered in the course of exhaustive research aimed at developing a novel resistance-type oxygen sensor which would allow a fundamental resolution of the various problems of prior art that in a resistance-type oxygen sensor in which the oxygen gas detection part comprises an oxide semiconductor, this aim could be achieved by using as the oxide semiconductor material an oxide comprising cerium ions and a specific concentration of hafnium ions, and perfected the present invention as a result of further research.

It is an object of the present invention to provide a resistance-type oxygen sensor having an oxygen gas detection part which uses an oxide with cerium ions as the principal component, and having lower resistivity of the oxygen semiconductor and lower temperature dependence of this resistivity than resistance-type oxygen sensors in which the oxygen gas detection part is made of cerium oxide only or of a solid solution of cerium oxide added with zirconium oxide. It is another object of the present invention to provide a resistance-type oxygen sensor with low resistivity and low temperature dependence. It is yet another object of the present invention to provide an oxygen sensor device to be used in air-fuel feedback control systems for optimizing the combustion efficiency of boilers and the like.

The present invention to solve the aforementioned problems is constituted by the following technical features.

(1) A resistance-type oxygen sensor which comprises, as a constituent element, an oxygen gas detection part made of an oxide semiconductor, characterized in that the oxide semiconductor is an oxide comprising cerium ions and hafnium ions, and the amount of substance of cerium ions as a percentage of the amount of substance of positive ions in the oxide semiconductor is 60 mol % or more.

(2) The resistance-type oxygen sensor according to above (1), wherein hafnium ions are in solid solution in the parent phase of said oxide semiconductor.

(3) The resistance-type oxygen sensor according to above (1) or (2), wherein the amount of substance of hafnium ions as a percentage of the amount of substance of positive ions in said oxide semiconductor is 3 to 30 mol %.

(4) The resistance-type oxygen sensor according to above (1) or (2), wherein the amount of substance of hafnium ions as a percentage of the amount of substance of positive ions in the oxide semiconductor is 6 to 10 mol %.

(5) The resistance-type oxygen sensor according to above (1) or (2), wherein the parent phase of the oxide semiconductor is a cubic crystal having a fluorite structure.

(6) The resistance-type oxygen sensor according to any of above (1) through (5), wherein the positive ions contained in the oxide semiconductor are only cerium ions and hafnium ions.

(7) The resistance-type oxygen sensor according to any of above (1) through (6), wherein the conductivity of the oxygen gas detection part made of the oxide semiconductor is at least $1\times10^{-4}$ S/cm at 600° C.

(8) The resistance-type oxygen sensor according to any of above (1) through (7), wherein the oxygen gas detection part made of the oxide semiconductor is a porous thick film.

(9) The resistance-type oxygen sensor according to above (5), wherein the oxygen gas detection part made of the oxide semiconductor has a film thickness of 50 μm or less, and the resistance thereof is 200 kΩ or less at 600° C. and an oxygen partial pressure of $1.8 \times 10^4$ Pa.

(10) The resistance-type oxygen sensor according to any of above (1) through (9), comprising a temperature compensation part for controlling the temperature dependency of the output which is connected serially as an electric circuit element to the oxygen gas detection part.

(11) The resistance-type oxygen sensor according to any of above (1) through (10), comprising a heater for controlling the temperature of the resistance-type oxygen sensor.

(12) An oxygen sensor device comprising the resistance-type oxygen sensor according to any of above (1) through (11) as a constituent element.

(13) The oxygen sensor device according to above (12), comprising an instrument capable of applying a fixed voltage and an instrument capable of measuring voltage.

(14) An air-fuel ratio feedback control system for controlling the air-fuel ratio of a combustion engine, comprising the resistance-type oxygen sensor according to any of above (1) through (11) as a constituent element.

(15) The air-fuel ratio feedback control system according to above (14), wherein the combustion engine is an automobile combustion engine.

(16) An automobile exhaust gas catalyst deterioration detection system, comprising the resistance-type oxygen sensor according to any of above (1) through (11).

The present invention is explained in more detail below.

In the resistance-type oxygen sensor of the present invention, the oxide semiconductor in a resistance-type oxygen sensor wherein the oxygen gas detection part is made of an oxide semiconductor is an oxide comprising cerium ions and hafnium ions, the amount of substance of cerium ions as a percentage of the amount of substance of positive ions in the aforementioned oxide semiconductor is 60 mol % or more, and the amount of substance of hafnium ions as a percentage of positive ions in the aforementioned oxide semiconductor (hereunder sometimes called the hafnium ion concentration) is 3 to 305 mol % or preferably 5 to 10 mol %.

The oxide semiconductor here is electronically conductive, and the oxygen ion transport number is near 0. Moreover, the effects of the present invention can be anticipated even if zirconium ions are included at a concentration which is no more than half the concentration of hafnium ions. Naturally, if the oxide semiconductor which is the oxygen gas detection part is a single phase, the hafnium ions are present in a solid solution. If there are multiple phases, the hafnium ions must be in solid solution in the parent phase of the oxide semiconductor. That is, the cerium oxide and hafnium oxide in the aforementioned oxide semiconductor are not simply in a mechanical mixture. Moreover, the parent phase of the oxide semiconductor is preferably a cubic crystal with a fluorite structure. Moreover, in the present invention the statement that the positive ions contained in the oxide semiconductor are only cerium ions and hafnium ions means that the concentration of specific positive ions other than cerium ions and hafnium ions is less than 1%.

One example of the structure of a resistance-type oxygen sensor of the present invention is shown in FIG. 1. In this resistance-type oxygen sensor, gas detection part 3, which comprises an oxide semiconductor, and temperature compensation part 4 for controlling the temperature dependence of the output are arranged on substrate 1, and electrodes 2 are arranged so as to supply electricity to gas detection part 3 and temperature compensation part 4. However, the structure of the resistance-type oxygen sensor of the present invention is not limited to that shown in FIG. 1, and can be designed in any way according to the type, size and intended use thereof.

Desirable forms of the oxygen gas detection part include for example a thick film or thin film, but are not limited to these. There are no particular limits on the method of preparing the oxygen gas detection part, but in the case of a thick film the film can be prepared by screen printing or the like.

To give a simple explanation, an oxide powder comprising cerium ions and hafnium ions is prepared in advance. The method of preparing the powder may be a sedimentation method or spray pyrolysis method, but is not limited to these. Another example is a method of mixing cerium oxide and hafnium oxide, solid-phase sintering them at high temperatures between 1400° C. and 1700° C. and pulverizing them. Next, the resulting powder is mixed with a vehicle or other organic solvent to prepare a paste. Next, the resulting paste is screen printed on a substrate, pre-baked at 400 to 600°C., and baked at 1050° C. to 1200° C. to obtain a thick film.

In the case of a thin film, the film can be prepared by a method such as MOCVD, sputtering, spin coating or the like. There are no particular limits on the raw material for preparing the oxygen gas detection part, and any raw materials may be used as long as the prepared oxygen gas detection part is an oxide comprising cerium ions and hafnium ions. If it is a thick film it is preferably a porous body.

The sensor of the present invention requires an electrode for measuring the resistance of the oxygen gas detection part. The electrode may be of a precious metal such as Pt, Pd or the like for example, but is not limited thereby. There are also no particular limits on the method of preparing the electrode, and any method or means may be used.

In the case of a resistance-type oxygen sensor with attached heater, a ceramic heater or the like is attached to the substrate for example. However, there are no particular limits on the attached position of the heater or the shape or properties of the heater. In this way it is possible to warm the sensor to any temperature between 600 and 1000° C. even if the exhaust gas is at a low temperature.

The oxygen sensor device of the present invention can be designed in any way with the resistance-type oxygen sensor of the present invention, an electrical circuit part and a sensor output or other display part as basic constituent elements. On example of the electrical circuit of this device is shown in FIG. 2. In this figure, the circuit of the heater part is omitted. The part within the dotted lines is the resistance-type oxygen sensor. In this resistance-type oxygen sensor, a gas detection part and a temperature compensation part are serially attached, a fixed voltage is applied, and the potential difference of the gas detection part is read as the sensor output.

The present invention provides an air-fuel ratio feedback control system for controlling the air-fuel ratio of a combustion engine. The air-fuel ratio here is the weight ratio of air to fuel, and there is a 1:1 correlation between the oxygen partial pressure and the air-fuel ratio. In the present invention, an automobile air-fuel ratio feedback control system can be designed and constructed as desired with for example the resistance-type oxygen sensor of the present invention, a flow meter for measuring the flow of air into the engine, a fuel injector for injecting fuel into the engine, and a control circuit for receiving signals from the oxygen sensor and fuel meter, performing calculations and controlling the amount of fuel injected by the fuel injector as basic constituent elements.

Moreover, in the present invention an air-fuel feedback control system for optimizing the combustion efficiency of a combustion engine can be designed and constructed as desired with for example the resistance-type oxygen sensor of the present invention, a flow meter for measuring the flow of air into the engine, a fuel injector for injecting fuel into the engine, and an electronic control unit for receiving signals from the oxygen sensor and fuel meter, performing calculations and sending output signals to the fuel control system as basic constituent elements.

Moreover, in the present invention an automobile exhaust gas catalyst deterioration detection system can be designed and constructed as desired with for example the resistance-type oxygen sensor of the present invention, an electronic control unit for reading signals from the oxygen sensor, performing calculations and determining whether the catalyst has deteriorated, and a display part for receiving signals from the electronic control unit and indicating whether the catalyst has deteriorated as basic constituent units.

With regard to the functions of the invention, in the present invention, it is thought that by adding hafnium to a gas detection part made of the oxide semiconductor cerium oxide, it is possible to reduce the resistivity of the oxygen gas detection part of a sensor while reducing temperature dependence, and this is attributed to changes in the electronic structure or defect concentration. That is, it is theorized that resistivity declines and temperature dependency is reduced as a result either of greater electron mobility due to changes in the electronic structure, or of increased electron concentration due to an increased amount of oxygen vacancies, or of both of these effects.

The particular effects of (1) providing a novel resistance-type oxygen sensor in a resistance-type oxygen sensor in which the oxygen gas detection part is made of an oxide semiconductor, the oxygen semiconductor is an oxide comprising cerium ions and hafnium ions, the hafnium ions are an oxide in solid solution in the principal phase, and the concentration of hafnium ions is 3 to 30 mol %, (2) allowing the sensor output reading circuit to be simplified, (3) allowing the resistivity of the oxygen gas detection part of the aforementioned sensor to be reduced and the temperature dependence to be reduced, and (4) providing an oxygen sensor device and an air-fuel ratio control system comprising the aforementioned circuit, are achieved by the present invention.

DESCRIPTION OF THE PREFERRED EMBODIMENTS

Next, the present invention is explained in detail based on examples, but the present invention is not limited by these examples.

EXAMPLE 1

Cerium oxide powder and hafnium oxide powder were measured out so that the ratio of cerium ions to hafnium ions was 9:1, and mixed in a wet system using an agate mortar and ethanol as the dispersion medium. After being mixed, the powder was dried and press molded to obtain a molded body. The molded body was baked for 10 hours in air at 1400° C., and solid-phase sintered. After being cooled to room temperature the sintered body was pulverized to obtain a powder. A paste of the resulting powder mixed with an organic solvent vehicle was screen printed on an aluminum oxide substrate on which a platinum comb-shaped electrode had been previously formed. Next, this was heated at 500° C. in air, and then heated in air at 1300° C. to obtain a thick film. The composition of the thick film was $Ce_{0.9}Hf_{0.1}O_2$.

Figure 1:
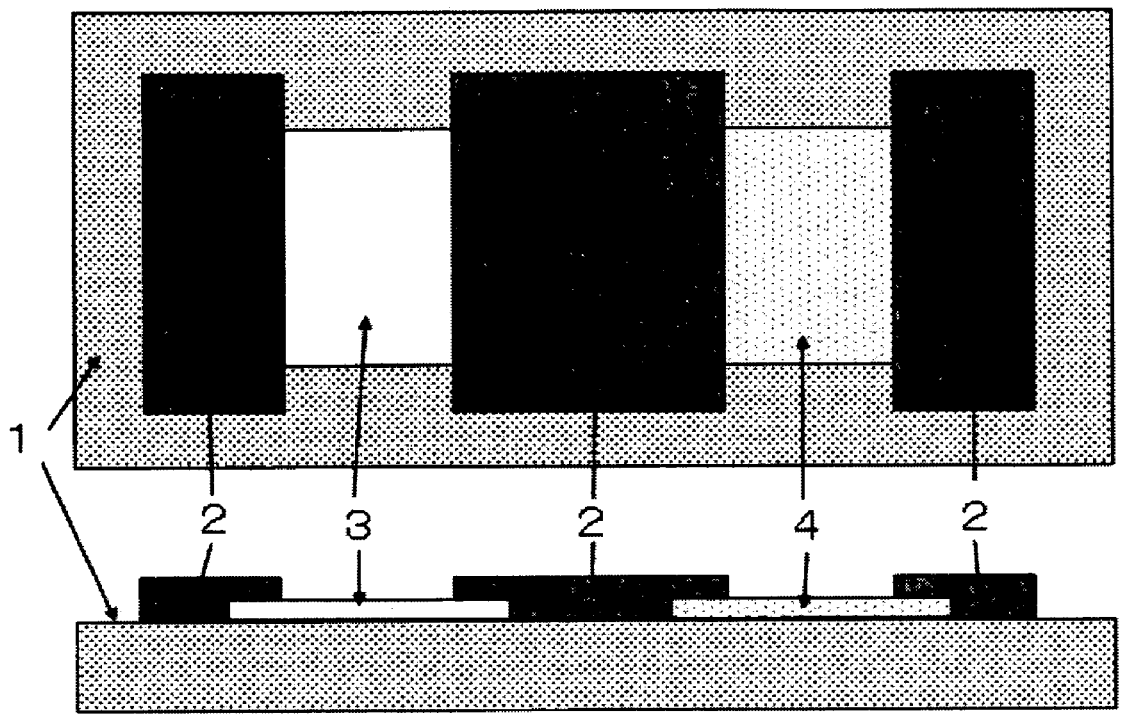
FIG. 1 is an outer view of the structure of a resistance-type oxygen sensor of the present invention.
Figure 2:
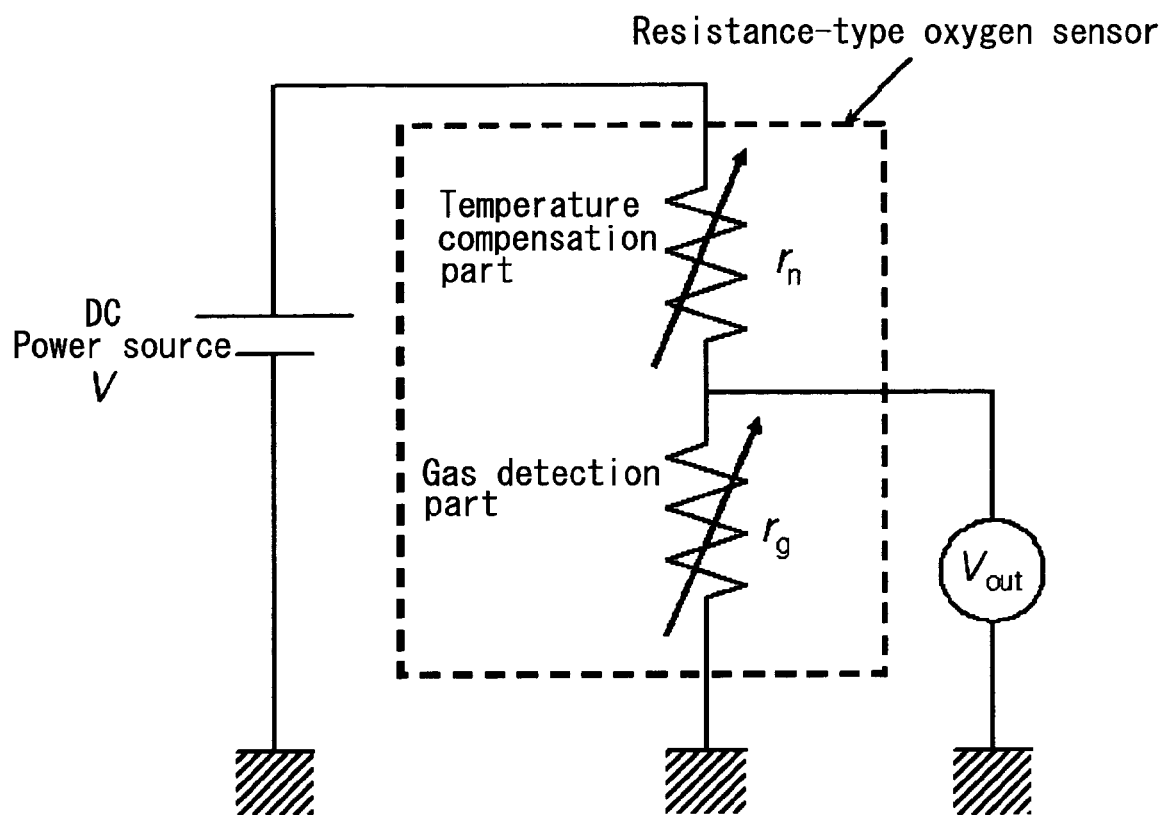
FIG. 2 is a circuit diagram showing the operations of an oxygen sensor device comprising the resistance-type oxygen sensor of the present invention.
Figure 3:
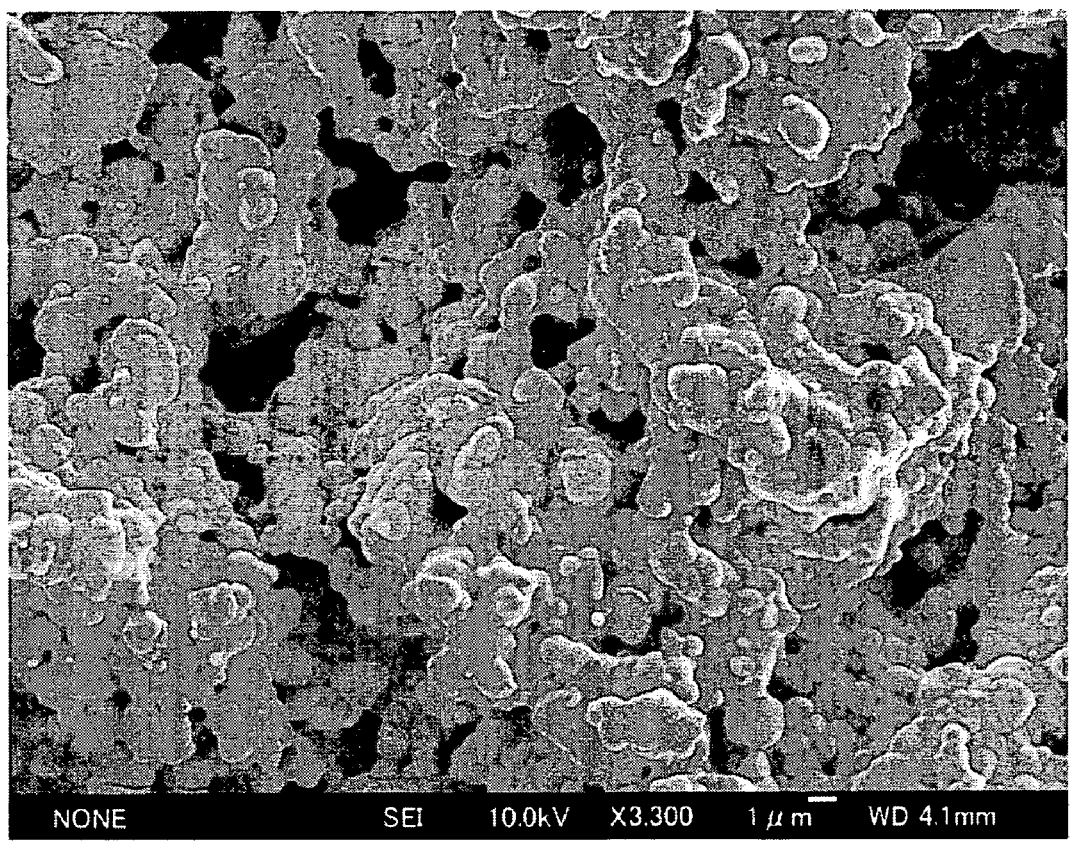
FIG. 3 is a scanning electron microscope image of the oxygen gas detection part of a resistance-type oxygen sensor using hafnium-added cerium oxide with a hafnium concentration of 10 mol % which was prepared by the methods given in Example 1.
Figure 4:
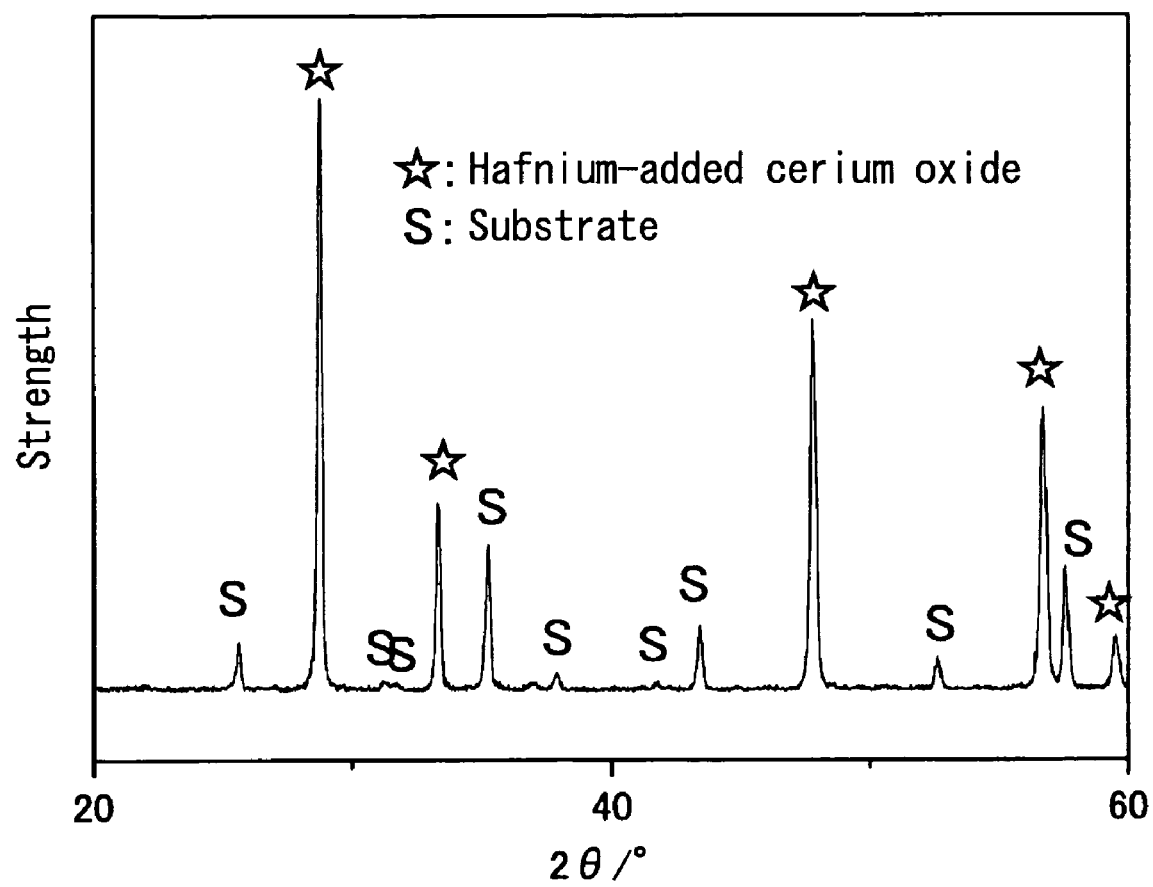
FIG. 4 shows x-ray diffraction results for the oxygen gas detection part of a resistance-type oxygen sensor using hafnium-added cerium oxide with a hafnium concentration of 10 mol % which was prepared by the methods given in Example 1.

The composition of the thick film after baking at 1300° C. was observed under a scanning electron microscope. The results are shown in FIG. 3. As shown in FIG. 3, this thick film was a porous body with a grain size of 1 to 2 µm. The film thickness was 20 µm. X-ray diffraction analysis of the thick film after baking showed that it was a single phase with hafnium ions in solid solution as shown in FIG. 4. This single phase had a fluorite structure.

Figure 5:
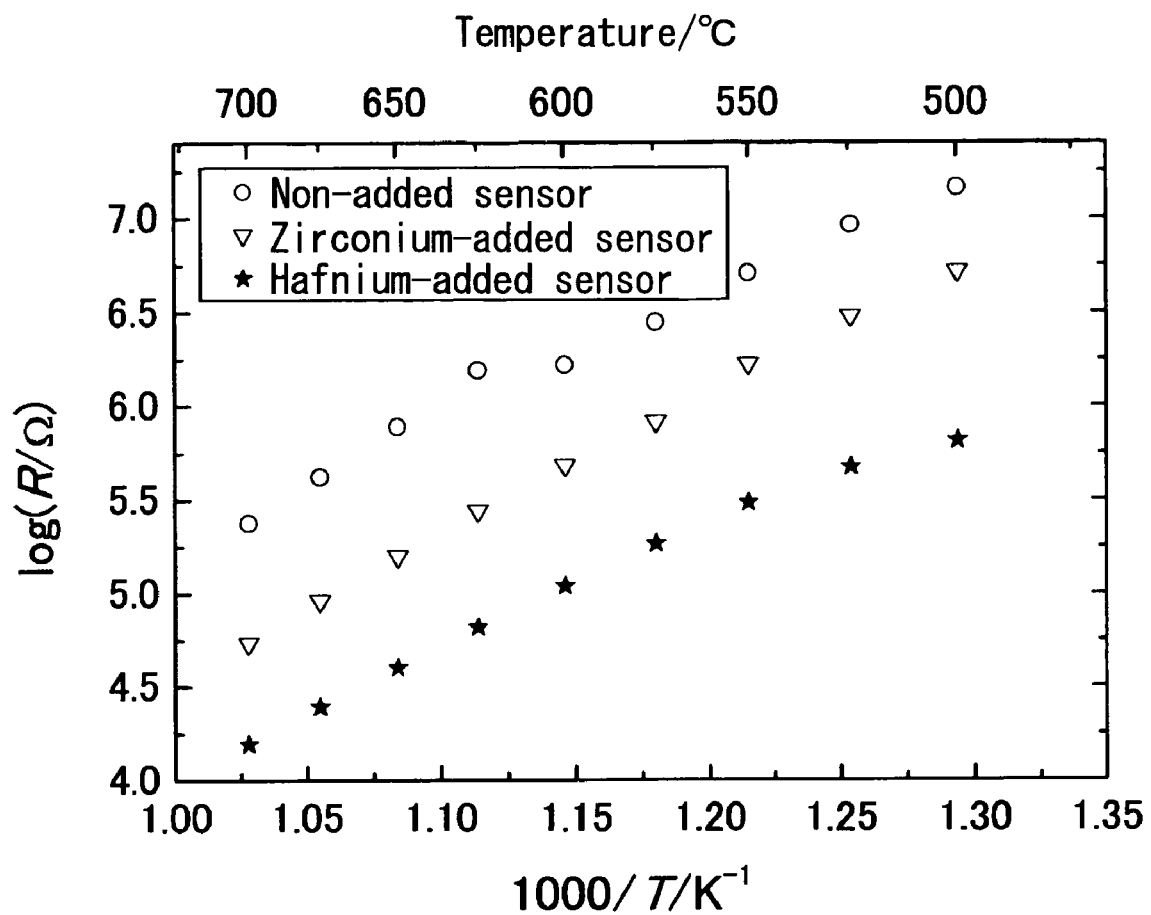
FIG. 5 shows the relationship between temperature and resistance of the oxygen gas detection part of a resistance-type oxygen sensor using hafnium-added cerium oxide with a hafnium concentration of 10 mol % (hafnium-added sensor) which was prepared by the methods given in Example 1. The results for a resistance-type oxygen sensor using cerium oxide with nothing added (non-added sensor) and a resistance-type oxygen sensor using zirconium-added cerium oxide with a zirconium ion concentration of 10 mol % (zirconium-added sensor) are shown as well as comparative examples. The oxygen partial pressure of the measurement atmosphere was $1.8 \times 10^4$ Pa.

The resistance of the oxygen gas detection part of a resistance-type oxygen sensor prepared by the aforementioned methods using hafnium-added cerium oxide with a hafnium ion concentration of 10 mol % (hereunder sometimes called the hafnium-added sensor) was measured at an oxygen partial pressure of $1.8 \times 10^4$ Pa in the range of 500 to 700° C. The results are shown in FIG. 5. The resistance values of the oxygen gas detection parts of a resistance-type oxygen sensor using cerium oxide with nothing added (hereunder sometimes called the non-added sensor) and a resistance-type oxygen sensor using zirconium-added cerium oxide with a zirconium ion concentration of 10 mol % (hereunder sometimes called the zirconium-added sensor) are also shown as comparative examples in FIG. 5. These resistance values were measured by the two-terminal method. These three different oxygen gas detection parts were the same in terms of shape and size and in terms of the shape and size of their platinum electrodes.

The resistance of the non-added sensor was greater than that of the zirconium added sensor, which was greater than that of the hafnium-added sensor, and at 600° C. (1000/T=1.145 $K^{-1}$), the resistance values of the hafnium-added sensor, the zirconium-added sensor and the non-added sensor were 0.11 MΩ, 0.48 MΩ and 1.7 MΩ, respectively. Thus, at 600° C. the resistance of the non-added sensor was 3.4 times that of the zirconium-added sensor and 15 times that of the hafnium-added sensor, confirming that the resistance-reducing effect of hafnium is much greater than that of zirconium.

Next, the temperature dependence of resistance between 500° C. and 700° C. is shown. Resistance R has the following relational expression:

$$R = R_0 \exp(E_a/kT)$$

(where $E_a$ is activation energy, $R_0$ is a constant, k is Boltzmann's constant and T is absolute temperature. Consequently, activation energy ($E_a$) can be used as an indicator of temperature dependence. The greater the $E_a$, the greater the temperature dependence.

TABLE 1

| | Activation energy (eV) | |
|---|---|---|
| | Oxygen partial pressure $1.8 \times 10^4$ Pa | Oxygen partial pressure $2.0 \times 10^2$ Pa |
| Non-added sensor | 1.30 | 1.46 |
| Zirconium-added sensor | 1.49 | 1.57 |
| Hafnium-added sensor | 1.24 | 1.28 |

As shown in Table 1, the $E_a$ value of the zirconium-added sensor was 0.1 eV or more greater than that of the non-added sensor. Meanwhile, the $E_a$ value of the hafnium sensor was 0.05 eV or more less than that of the non-added sensor. Thus, by adding hafnium it was possible to reduce the activation energy or in other words to reduce temperature dependency below that achieved when nothing or zirconium was added.

Figure 6:
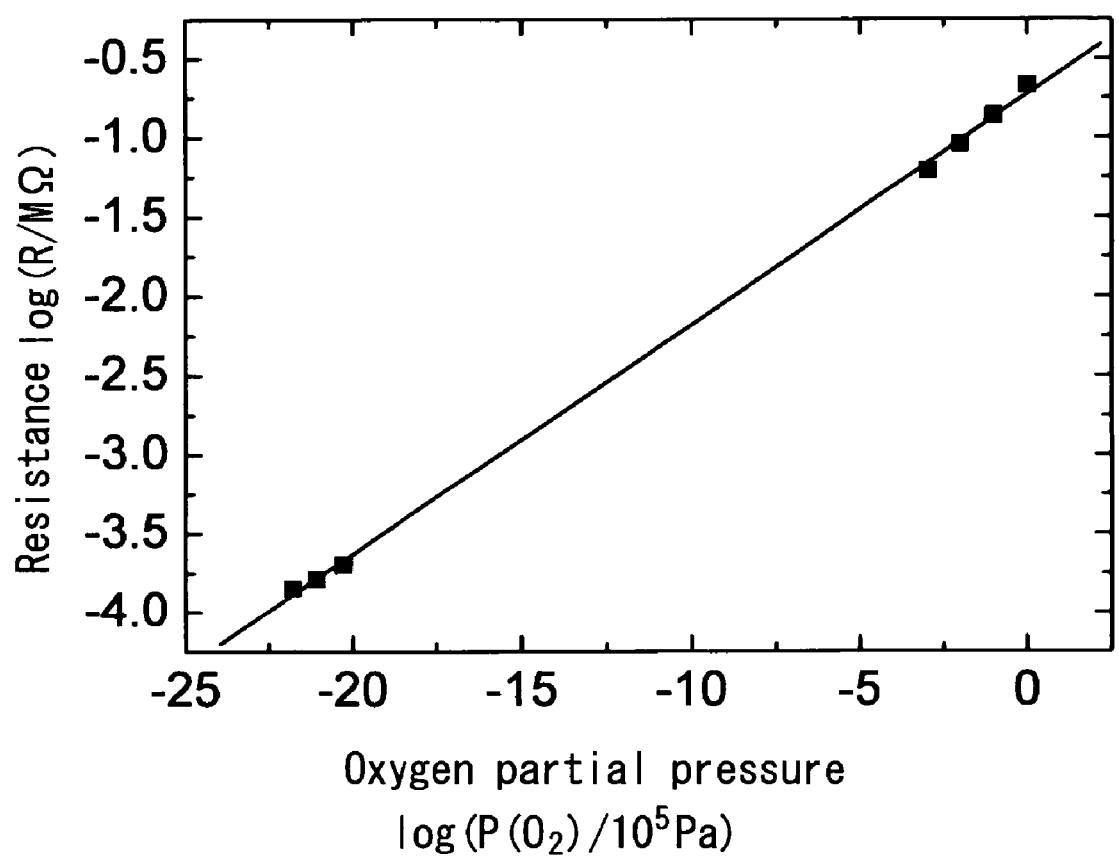
FIG. 6 shows the relationship between oxygen partial pressure and resistance of the oxygen gas detection part of a resistance-type oxygen sensor using hafnium-added cerium oxide with a hafnium concentration of 10 mol % (hafnium-added sensor) which was prepared by the methods given in Example 1.

FIG. 6 shows the relationship between oxygen partial pressure and resistance of the oxygen gas detection part of a hafnium-added sensor. A linear relationship is obtained within a wide range of oxygen partial pressures, showing that it can be used as an oxygen sensor at oxygen partial pressures ranging from high oxygen to low oxygen. The reaction speed of the hafnium-added sensor was similar to that of the zirconium-added sensor.

EXAMPLE 2

Thick films were prepared as the oxygen gas detection parts by methods similar to those used in Example 1 with varying concentrations of hafnium, and resistance-type oxygen sensors were prepared. The prepared thick films had a composition of $Ce_{1-x}Hf_xO_2$, with x values of 0.01, 0.02, 0.05, 0.07, 0.10, 0.15, 0.20, 0.30 and 0.50, and the corresponding concentrations of hafnium ions as a percentage of positive ions were 1, 2, 5, 7, 10, 15, 20, 30 and 50 mol %.

Figure 7:
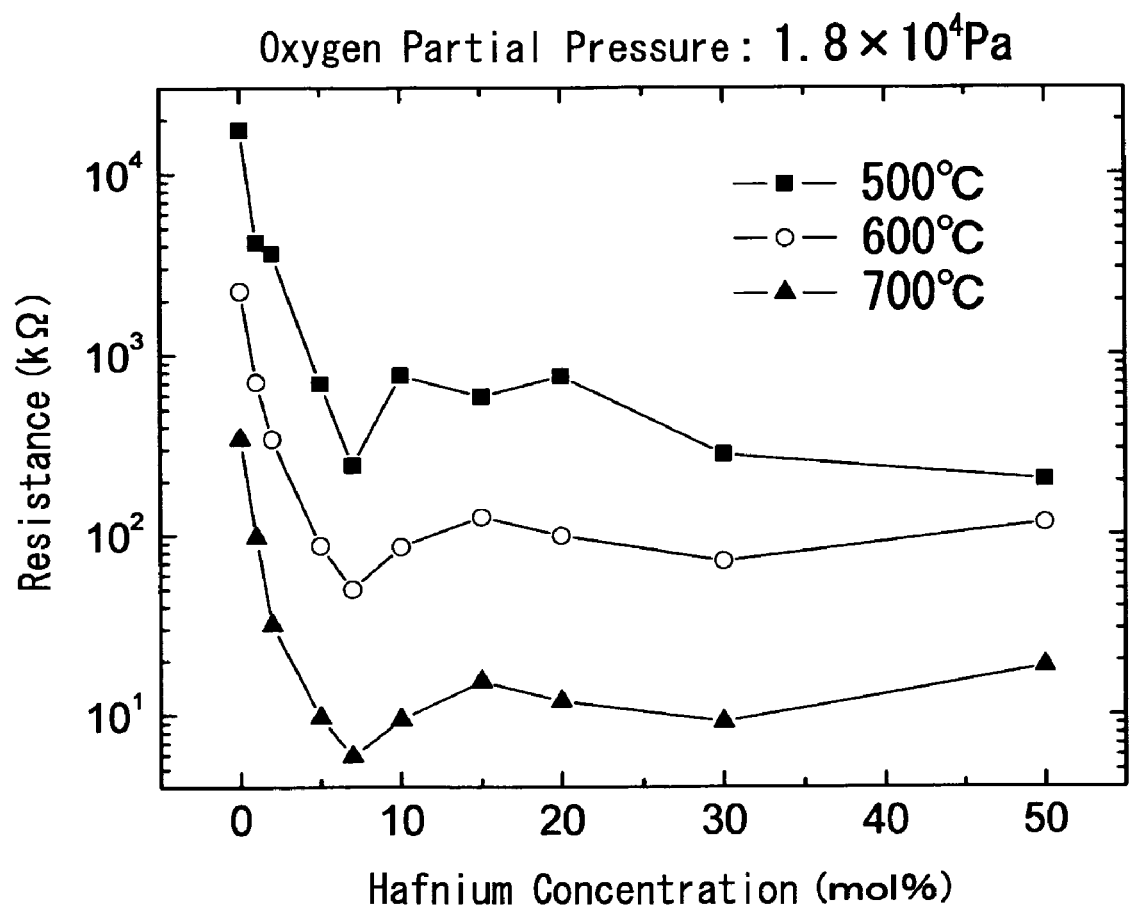
FIG. 7 shows resistance of the oxygen gas detection parts of resistance-type oxygen sensors prepared in Example 2 at temperatures of 500, 600 and 700° C. and an oxygen partial pressure of $1.8 \times 10^4$ Pa.

FIG. 7 shows resistance between electrodes in the thick films at 500, 600 and 700° C. and an oxygen partial pressure of $1.8 \times 10^4$ Pa. Up to a hafnium ion concentration of 7 mol %, resistance decreased dramatically as the hafnium ion concentration increased. Resistance at a hafnium ion concentration of 3 mol % was smaller by a factor of more than 10 than at a hafnium ion concentration of 0 mol %. Between a hafnium ion concentration of 7 and about 15 mol %, however, resistance increased as the hafnium ion concentration increased.

However, the resistance of the thick film at a hafnium ion concentration of around 15 mol % was about the same as at a hafnium ion concentration of 5 mol %. Between a hafnium ion concentration of about 15 mol % and about 30 mol %, resistance declined gradually as the hafnium ion concentration increased. At a hafnium ion concentration of about 50 mol %, the problem was that the resistance value was not stable at low oxygen partial pressure. From this it was concluded that at a hafnium ion concentration of between 3 mol % and 30 mol % the resistance-reducing effect was greatest, and resistance could be measured easily.

Figure 8:
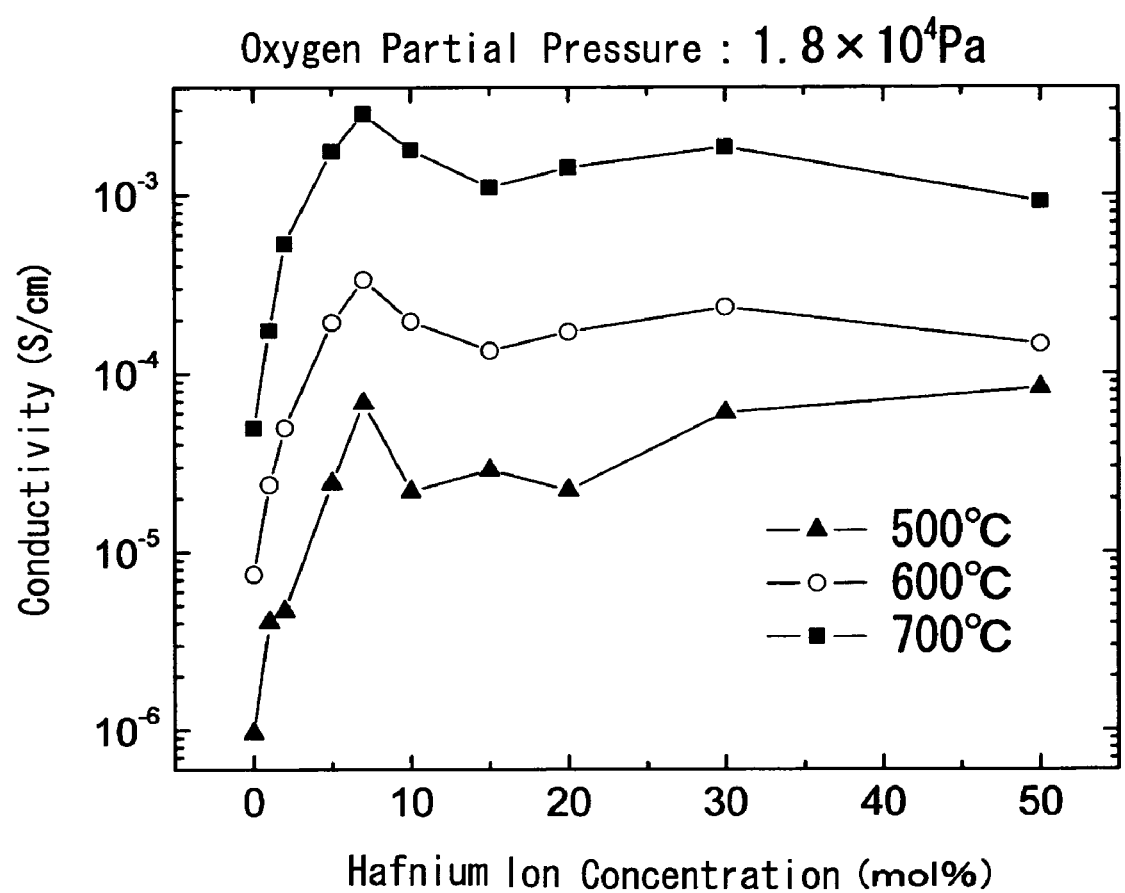
FIG. 8 shows conductivity of the oxygen gas detection parts of resistance-type oxygen sensors prepared in Example 2 at temperatures of 500, 600 and 700° C. and an oxygen partial pressure of $1.8 \times 10^4$ Pa.

Conductivity at a hafnium ion concentration of 0 mol % or in other words the conductivity of $CeO_2$ has been reported by S. Roitti and V. Longo (*Ceramurigia* 2, 97 (1972). According to this, the conductivity in air at 600° C. is $7.5 \times 10^{-6}$ S/cm. Using this data, the conductivity values of each sample at 500, 600 and 700° C. were calculated from the resistance values shown in FIG. 7. The results are shown in FIG. 8. The conductivity values here are for total conductivity including both bulk and intergranular. Above a hafnium ion concentration of 3 mol %, conductivity was $1 \times 10^{-4}$ or more at 600° C.

Looking at activation energy as an indicator of the temperature dependence of resistance, activation energy tended to be greater at hafnium ion concentrations of between 1 and 5 mol % than at a hafnium ion concentration of 0 mol %. It was therefore concluded that 6 mol % or more is a preferable hafnium ion concentration.

Figure 9:
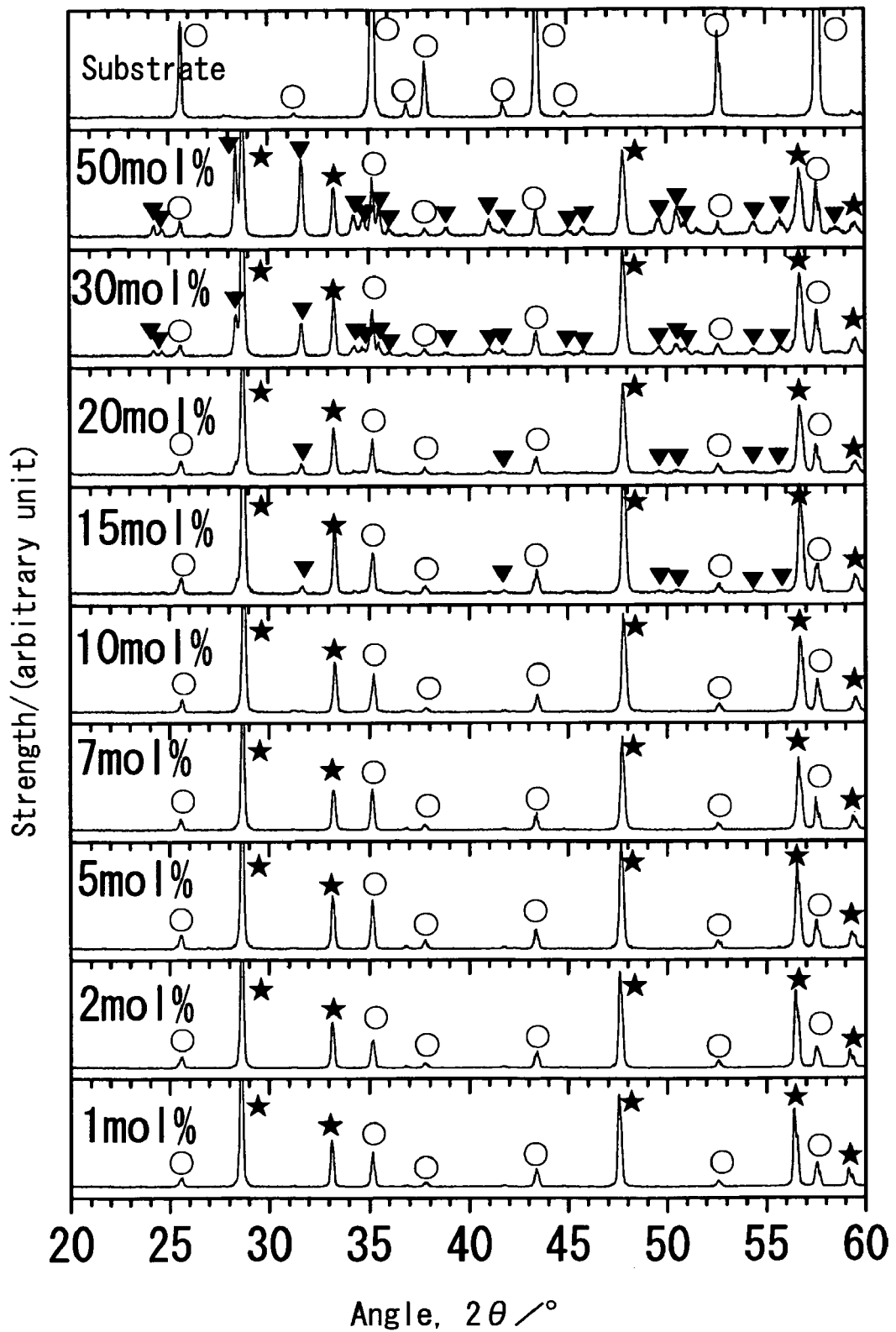
FIG. 9 shows the XRD patterns of thick films which are the oxygen gas detection parts of the resistance-type oxygen sensors prepared in Example 2. ★, ▼ and ○ indicate the peaks of the cubic crystals, monoclinic crystals and substrate, respectively. Mol % in the figure indicates hafnium ion concentration.

Next, the XRD patterns of the thick films prepared in Example 2 are shown in FIG. 9. Because they were analyzed with the substrate, peaks from the substrate are included in each pattern. Consequently, the peaks from the substrate can be discounted when considering the phase relationships of the thick films. Between a hafnium ion concentration of 0 mol % and 10 mol %, only cubic crystal peaks were observed. This confirms that within this concentration range, the thick film is a single phase of cubic crystals.

Above a hafnium ion concentration of 10 mol %, peaks from monoclinic hafnia crystals were precipitated as a second phase in addition to the cubic crystal peaks. This confirms the existence of a mixed two-phase system of cubic crystals and monoclinic crystals. Because long-term stability may be deficient in the case of a two-phase mixture, a single phase is more desirable. It was therefore concluded that a hafnium ion concentration of 10 mol % or less is preferable.

EXAMPLE 3

Figure 10:
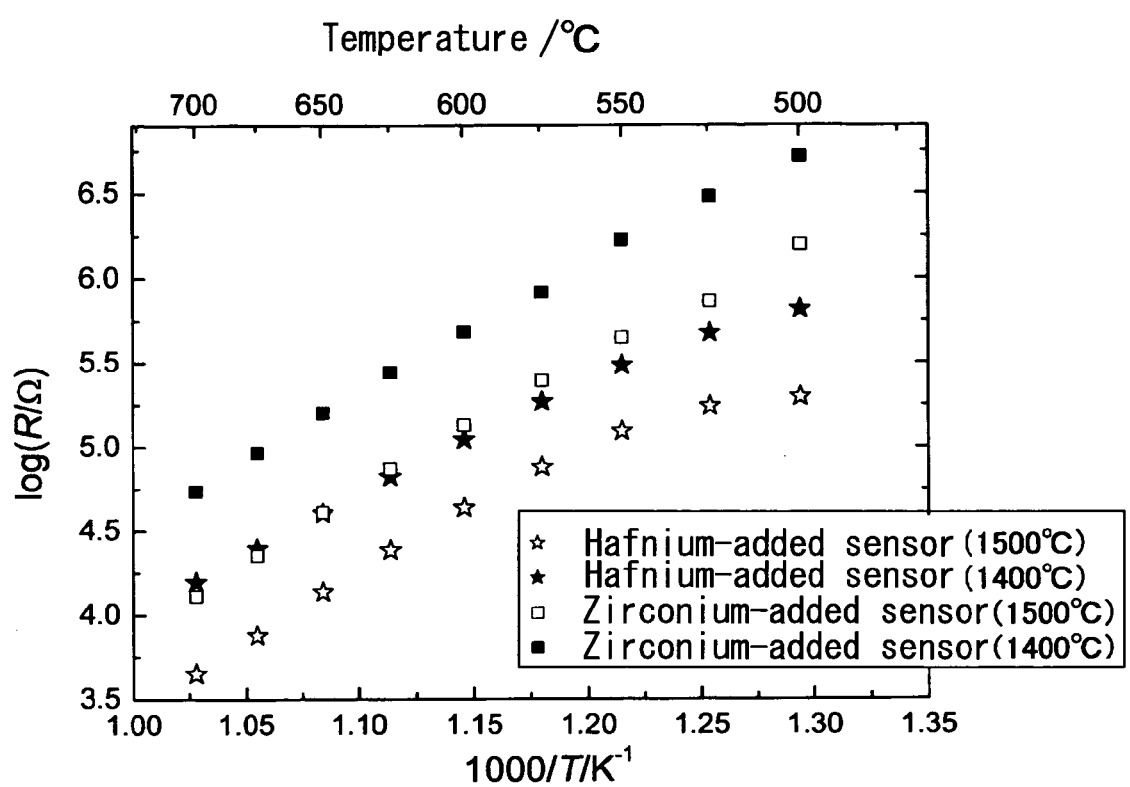
FIG. 10 shows the relation between resistance and temperature of the hafnium-added sensor (1500° C.), which is prepared by the same method as shown in the Example 3.

The relation between the resistance and temperature of the hafnium-added sensor, which is prepared by using the powder produced by the same conditions as that of the method of the example 1, except that the sintering temperature of the molded body is changed to 1500° C., is shown in FIG. 10. The results of the comparative example and example 1 are also shown in the figure. In FIG. 10, the hafnium-added sensor in which the sintering temperatures of the molded bodies are 1500° C. and 1400° C. are described as the hafnium-added sensor (1500° C.) and the hafnium-added sensor (1400° C.) respectively, and the zirconium-added sensor in which the sintering temperatures of the molded bodies are 1500° C. and 1400° C. are described as the zirconium-added sensor (1500° C.) and the zirconium-added sensor (1400° C.) respectively. It is revealed that in the case of the sintering temperature of the molded body is 1500° C., the resistance of the sensor becomes smaller in a half figure compared with that of the comparative example.

Further, it is revealed that in the case in which the sintering temperatures of the molded bodies are same conditions, the resistance of the hafnium-added sensor is smaller than that of the zirconium-added sensor.

As described above, the present invention relates to a resistance-type oxygen sensor and an air-fuel ratio control system using that sensor, and with the present invention it is possible to provide, in a resistance-type oxygen sensor in which the oxygen gas detection part is made of an oxygen semiconductor, a new type of resistance-type oxygen sensor wherein the oxygen semiconductor is an oxide comprising cerium ions and hafnium ions and is an oxide in which the hafnium ions are in solid solution in the principal phase, with the concentration of hafnium ions being 3 to 30 mol %. The sensor output reading circuit can be simplified in the present invention. The resistivity of the oxygen gas detection part of the aforementioned sensor can be reduced, as can temperature dependency. The present invention can provide an oxygen sensor device and an air-fuel ratio control system using the aforementioned sensor.

What is claimed is:

1. A resistance-type oxygen sensor, comprising:
an oxygen gas detection part made of an oxide semiconductor, wherein the oxide semiconductor is an oxide comprising cerium ions and hafnium ions,
the amount of the cerium ions as a percentage of the amount of positive ions in the oxide semiconductor is 60 mol % or greater,
the hafnium ions are in a solid solution in a parent phase of said oxide semiconductor,
the amount of the hafnium ions as a percentage of the amount of the positive ions in said oxide semiconductor is 3 to 30 mol %,
the conductivity of the oxygen gas detection part made of the oxide semiconductor is at least $1\times10^{-4}$ S/cm at 600° C., and
the oxide semiconductor has a film thickness of 50 μm or less, a resistance of 200 kΩ or less at 600° C. and an oxygen partial pressure of $1.8\times10^{4}$ Pa.

2. The resistance-type oxygen sensor according to claim 1, wherein the amount of the hafnium ions as a percentage of the amount of the positive ions in the oxide semiconductor is 6 to 10 mol %.

3. The resistance-type oxygen sensor according to claim 1, wherein the parent phase of the oxide semiconductor is a cubic crystal having a fluorite structure.

4. The resistance-type oxygen sensor according to claim 1, wherein the positive ions contained in the oxide semiconductor are only the cerium ions and the hafnium ions.

5. The resistance-type oxygen sensor according to claim 1, wherein the oxygen gas detection part made of the oxide semiconductor is a porous thick film.

6. The resistance-type oxygen sensor according to claim 1, wherein said resistance-type oxygen sensor has a temperature compensation part for controlling a temperature dependency of the output which is connected serially as an electric circuit element to the oxygen gas detection part.

7. The resistance-type oxygen sensor according to claim 1, wherein said resistance-type oxygen sensor has a heater for controlling a temperature of the sensor.

* * * * *